US010849509B2

(12) United States Patent
Zhang

(10) Patent No.: US 10,849,509 B2
(45) Date of Patent: Dec. 1, 2020

(54) PATIENT SIGNAL FILTERING

(71) Applicant: Siemens Medical Solutions USA, Inc., Malvern, PA (US)

(72) Inventor: Hongxuan Zhang, Palatine, IL (US)

(73) Assignee: Siemens Healthcare GmbH, Erlangen (DE)

( * ) Notice: Subject to any disclaimer, the term of this patent is extended or adjusted under 35 U.S.C. 154(b) by 1583 days.

(21) Appl. No.: 14/549,670

(22) Filed: Nov. 21, 2014

(65) Prior Publication Data

US 2016/0143543 A1    May 26, 2016

(51) Int. Cl.
*A61B 5/00* (2006.01)
*A61B 5/021* (2006.01)
*A61B 5/04* (2006.01)
*A61B 5/0402* (2006.01)

(52) U.S. Cl.
CPC .......... *A61B 5/021* (2013.01); *A61B 5/04014* (2013.01); *A61B 5/0402* (2013.01); *A61B 5/726* (2013.01)

(58) Field of Classification Search
None
See application file for complete search history.

(56) References Cited

U.S. PATENT DOCUMENTS

| | | | |
|---|---|---|---|
| 3,967,102 A | 6/1976 | McCown | |
| 4,216,779 A * | 8/1980 | Squires | A61B 5/02208 128/900 |
| 4,513,254 A | 4/1985 | Harr | |
| 5,231,990 A * | 8/1993 | Gauglitz | A61B 5/0006 600/509 |
| 5,913,826 A * | 6/1999 | Blank | A61B 5/02007 600/500 |
| 5,929,699 A | 7/1999 | Lewicki | |
| 6,032,166 A | 2/2000 | Signell et al. | |
| 6,405,227 B1 | 6/2002 | Prakash | |
| 6,593,802 B2 | 7/2003 | Mariani et al. | |
| 6,636,128 B2 | 10/2003 | Rauscher | |
| 6,646,498 B2 | 11/2003 | Mohieldin et al. | |
| 6,677,814 B2 | 1/2004 | Low et al. | |
| 7,024,006 B1 | 4/2006 | Schwartz et al. | |
| 7,212,068 B2 | 5/2007 | Onody | |

(Continued)

OTHER PUBLICATIONS

Angelo Accetta, Sensorless Control of PMSM Fractional Horsepower Drives by Signal injection and Neural Adaptive-Band Filtering, Mar. 2012, IEEE Transactions on Industrial Electronics, vol. 59 No. 3, pp. 1355-1366.*

(Continued)

*Primary Examiner* — Christian Jang
*Assistant Examiner* — Sarah R Kingsley

(57) ABSTRACT

Disclosed herein is a framework for facilitating patient signal filtering. In accordance with one aspect, the framework performs a signature cycle matching pursuit method to remove a first signal component from a combination patient signal and generate a first output signal. Sub-bandwidth filtering of the first output signal may be performed to remove a second signal component and generate a second output signal. The framework may further remove a third signal component from the second output signal to generate a third output signal. A signal of interest may then be reconstructed based on the third output signal.

17 Claims, 9 Drawing Sheets

(56) References Cited

U.S. PATENT DOCUMENTS

| | | | | |
|---|---|---|---|---|
| 2003/0078505 | A1* | 4/2003 | Kim | A61B 5/0008 |
| | | | | 600/485 |
| 2005/0007091 | A1* | 1/2005 | Makeig | A61B 5/048 |
| | | | | 324/76.13 |
| 2006/0062405 | A1 | 3/2006 | McKee Cooper | |
| 2006/0153404 | A1 | 7/2006 | Gardner | |
| 2007/0253577 | A1 | 11/2007 | Yen et al. | |
| 2010/0060350 | A1* | 3/2010 | Zhang | H03H 11/1291 |
| | | | | 327/553 |
| 2011/0301473 | A1* | 12/2011 | Wariar | A61B 7/04 |
| | | | | 600/486 |
| 2012/0283583 | A1* | 11/2012 | Batkin | A61B 5/0225 |
| | | | | 600/493 |
| 2013/0096394 | A1* | 4/2013 | Gupta | A61B 5/04012 |
| | | | | 600/301 |

OTHER PUBLICATIONS

Thomas J. Dorsett, Application of a Prediction and Smoothing Algorithm to Non-Invasive Blood Pressure Measurement, 1991, Annual International Conference of the IEEE Engineering in Medicine and Biology Society, vol. 13 No. 1, pp. 0468-0469.*

Reza Sameni, A Review of Fetal ECG Signal Processing; Issues and Promising Directions, Jan. 1 2010, Open Pacing Electrophysiol Ther. J. 3, pp. 1-42.*

Parisa Akbary, Removing Power Line Interference and ECG Signal from EMG Signal Using Matching Pursuit, Oct. 2010, Signal Processing (ICSP), 2010 IEEE 10th International Conference on, pp. 1714-1717.*

Electrophysiology, Aug. 18, 2013, Wikipedia.*

Manuja Sharma, Cuff-Less and Continuous Blood Pressure Monitoring: A Methodological Review, May 9, 2017, Technologies, 5, 21, pp. 1-22 (Year: 2017).*

Jian-Qiang Li, Design of a Continuous Blood Pressure Measurement System Based on Pulse Wave and ECG Signals, Sep. 30, 2017, Cardiovascular Devices and Systems, 6, pp. 1-14 (Year: 2017).*

R.R. R Magavi, Estimation of Mean Arterial Pressure from ECG and BP using Mathematical Model, Apr. 2016, IJAREEIE, vol. 5 Issue 4, pp. 3352-3358 (Year: 2016).*

M.K. Ali Hassan, Measuring of Systolic Blood pressure Based on Heart Rate, 2008, IFMBE Proceedings vol. 21, pp. 595-598 (Year: 2008).*

Monika Simjanoska, Non-Invasive Blood Pressure Estimation from ECG Using Machine Learning Techniques, 2018, Sensors, 18, pp. 1-20 (Year: 2018).*

Gendy Monroy Estrada, Relationship of blood pressure with the electrical signal of the heart using signal processing, Nov. 30, 2014, TECCIENCIA, vol. 9, pp. 9-14 (Year: 2014).*

Dianne Pickering, Sue Stevens, How to measure and record blood pressure, 2013, Community Eye Health, 26(84): 76, pp. 1-4 (Year: 2013).*

Heart Rate and Blood Pressure: What's the Difference?, 2018, Heart and Vascular Institute, pp. 1-2 (Year: 2018).*

Blood Pressure vs. Heart Rate (Pulse), 2016, American Heart Association, pp. 1-3 (Year: 2016).*

Electrocardiogram (ECG or EKG), Jul. 31, 2015, American Heart Association, pp. 1 (Year: 2015).*

Electrocardiogram (ECG or EKG), Feb. 27, 2019, Mayo Clinic, pp. 1-7 (Year: 2019).*

Mallet, et al., "Matching Pursuits with Time-Frequency Dictionaries", IEEE Transactions on Signal Processing 1993:3397-3415.

* cited by examiner

PATIENT SIGNAL FILTERING

TECHNICAL FIELD

The present disclosure generally relates to systems and methods for filtering patient signals.

BACKGROUND

Filter technologies are crucial in yielding high quality signals, especially in medical patient signal acquisition where signals are at the millivolt level. Patient signals, such as surface electrocardiogram (ECG) signals, intra-cardiac electrogram (ICEG) signals or oximetric (e.g., SPO2) signals, are usually a combination of different patient responses, such as ECG voltage potentials, respiration potential, blood pressure signal, patient moving voltage signal, biological noise (e.g., due to cough, medicine, etc.), and so forth. Accordingly, the patient signals acquired from any kind of patient sensors or transducers are actually an integration of multiple signals and voltage potentials from different parts or functions of patient body.

Theoretically, each of these patient signals can be captured by using a sensor. However, a lot of patient risk and clinical procedure complexity may result from using too many types of sensors and transducers. For example, too many catheters and wires, such as intra-cardiac catheters for EP signal, IBP signal, temperature signal, ablation treatment-measurement, etc., may need to be inserted into the blood vessels.

In addition, signal acquisition designs typically process a gamut of noise sources that are varied in amplitude and frequency, such as patient moving noise, power line electrical noise, electrical and magnetic noise from other medical instruments in hospitals, etc. to resolve a clean signal from the input source. Current known clinical methods usually focus on envelop extraction and amplitude analysis, which may not be able to avoid the different types of noise, such as cough-respiration noise, electrical clutter noise, etc.

Known filter systems for clinical signals use fixed frequency bandwidth control, such as a low pass filter to eliminate high frequency noise and white noise, a high pass filter to remove signal shifting due to patient respiration, etc. However, most patient signals cannot be extracted by such fixed frequency system. Simple band stop and band pass filters cannot accurately extract, for example, blood pressure signal component from patient signals, since the frequency bandwidth of the blood pressure signal overlaps with other signals, such as ECG signal, patient moving signal, patient evoked potentials, motor evoked potential signals, etc.

The frequency bandwidth of blood pressure signals is typically between 5 to 50 Hz. However, blood pressure signal bandwidth may vary from case to case and from time to time during an on-going clinical case, depending on, for example, the heart rate. Blood pressure signal frequency bandwidth changes are usually nonlinear, and may present dynamic shifting and fluctuations. Known technologies cannot accommodate such nonlinear changes. In addition, known clinical methods for blood pressure acquisition and diagnosis are not able to reliably eliminate dynamic voltage offset noise and shifting effects from ablation and other electrical devices' noise on the patient body, which may affect the blood pressure waveform characterization.

SUMMARY

The present disclosure relates to a framework for facilitating patient signal filtering. In accordance with one aspect, the framework performs a signature cycle matching pursuit method to remove a first signal component from a combination patient signal and generate a first output signal. Sub-bandwidth filtering of the first output signal may be performed to remove a second signal component and generate a second output signal. The framework may further remove a third signal component from the second output signal to generate a third output signal. A signal of interest may then be reconstructed based on the third output signal.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

Figure 1A:
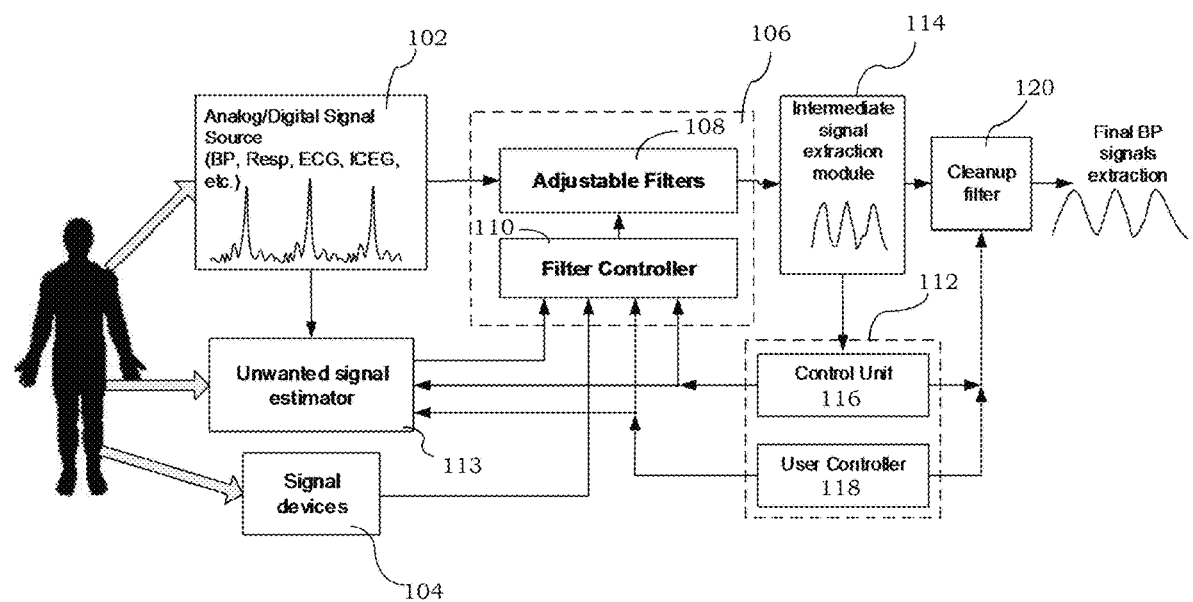
FIG. 1a shows an exemplary system.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

It is to be understood that the system and methods described herein may be implemented in various forms of hardware, software, firmware, special purpose processors, or a combination thereof. Preferably, the present invention is implemented in software as an application (e.g., n-tier application) comprising program instructions that are tangibly embodied on one or more program storage devices (e.g., magnetic floppy disk, RAM, CD ROM, ROM, etc.), and executable by any device or machine comprising suitable architecture. If written in a programming language conforming to a recognized standard, sequences of instructions designed to implement the methods can be compiled for execution on a variety of hardware platforms and for interface to a variety of operating systems. In addition, embodiments of the present framework are not described with reference to any particular programming language. It will be appreciated that a variety of programming languages may be used to implement embodiments of the present invention.

In accordance with one aspect, an adaptive and general-purpose multi-bandwidth filtering system is provided for automatically identifying a signal of interest (e.g., blood pressure signal) from a time-varying combination of patient signals. The system may advantageously adapt to changes in both signal and noise frequencies and amplitudes, such as heart rate, coughing noise, stimulation pacing noise, etc., with improved signal-to-noise ratios. The present framework may be applied to filter noisy signals and adapt to shifting noise frequencies. For example, in power line noise filtering, if the mains frequency drifts to 60.1 or 59.9 Hz, the filters that cut out mains noise and its harmonics can change their center frequencies to completely filter the noise. Many filters today cannot adapt to such changes, and therefore allows noise to pass under such circumstances. The present framework may use real time closed-loop signal component diagnosis to adaptively filter out noise and unwanted signals. Improvements in quality and reliability in medical signal acquisition may be achieved to facilitate medical professionals in providing more accurate diagnosis and treatment.

Some implementations of the present framework provide a methodology to extract a blood pressure signal component from electrophysiological (EP) patient signals. The framework removes unwanted signals (e.g., respiration signal, noise, ECG signal, etc.) from the EP patient signals. Although there are many methods to acquire and extract blood pressure signals from the patient's body, such as by using dedicated blood pressure cuffs, blood pressure catheter and transducers, etc., most of these clinical approaches need some hardware and additional device support (e.g., sensors, transducers, converters, etc.). The present framework may be applied to extract a blood pressure signal component from patient signals acquired by a single EP lead or signal channel sensor. This framework may also be implemented as a hemo-leadless or cuffless system for blood pressure (BP) measurement and real time BP signal monitoring.

For purposes of illustration, the present framework is described in the context of extracting blood pressure signals from patient signals. However, it should be appreciated that other signals of interest may also be extracted from a combination of patient signals. For example, ECG signals may be extracted from invasive blood pressure signals, respiration signals may be extracted from oximetric (or SPO2) signals, and so forth. These and other features, applications and advantages will be described in more details herein.

FIG. 1a shows an exemplary system 100 for implementing a method and system of the present disclosure. It is to be understood that, because some of the constituent system components and method steps depicted in the accompanying figures can be implemented in software, the actual connections between the system components (or the process steps) may differ depending upon the manner in which the present framework is programmed. For example, the system 100 may be implemented in a client-server, peer-to-peer (P2P) or master/slave configuration. In such configurations, the system 100 may be communicatively coupled to other systems or components via a network, such as an Intranet, a local area network (LAN), a wide area network (WAN), a P2P network, a global computer network (e.g., Internet), a wireless communications network, or any combination thereof. Given the teachings of the present framework provided herein, one of ordinary skill in the related art will be able to contemplate these and similar implementations or configurations.

Exemplary system 100 may include a signal source 102, signal devices 104, filter module 106 and various functional components (112, 113, 114 and 120). Signal source 102 may include an analog or digital sensor and transducer system (e.g., a single EP lead and signal channel sensor) that acquires a combination of patient signal components (or combination patient signal), such as blood pressure, respiration, ECG, ICEG signal components, etc. Such patient signal components may be combined with patient movement noise, electrical noise, artifacts from the power line and/or other signal devices 104, etc. Signal devices 104 may include a patient stimulator, ablator, electrical cutter, etc. For purposes of illustration, the combination patient signal is described herein as being composed of three signal components: blood pressure signal component, ECG signal component (>90% of the whole acquired signal) and respiration signal component. However, it should be appreciated that other types or number of signal components may also be included in the combination patient signal. The combination patient signal may be acquired via, for example, a single surface ECG lead.

Filter module 106 includes adjustable filters 108 and filter controller 110 that are used to filter the combination patient signal data from the signal source 102. An adjustable filter 108 may be one or more hardware, software and/or firmware components configured to remove from the combination patient signal data some unwanted components or features. The overall characteristics of the adjustable filters 108 may be modified by filter controller 110. Filter controller 110 may include various writable registers (analogue or digital) that store data that can be quickly retrieved to modify the parameter (e.g., frequency bandwidth, amplitude, etc.) of adjustable filters 108. In addition, filter controller 110 may adapt the adjustable filters 108 to new conditions by using, for example, a field-programmable gate array (FPGA) or a microprocessor capable of receiving filter feedback and sending data to the filter controller 110.

Adaptive control module 112 includes a control unit 116 and a user controller 118 for controlling the functioning of the filter module 106, the cleanup filter controller 120 and the unwanted signal estimator 113. The control unit 116 may provide real-time control parameter and/or noise evaluation. The user controller 118 may provide a user interface that enables a user to manually adjust the filter control parameters. Control unit 116 may continually check to determine if the conditions to switch the control parameters of the filters 108 are met. If they are met, filter control parameters are adjusted to modify the relevant filter's parameters (e.g., center frequency, bandwidth, spectrum amplitude, etc.). Alternatively, the user may manually control the filter parameters via a user interface provided by user controller 118.

A closed-loop feedback system may be provided for signal extraction. The filter module 106 and the various functional modules (112, 113, 114 and 120) may be implemented by one or more computer systems that are communicatively coupled to the signal source 102 and signal devices 104. Each computer system may include a processor device, non-transitory computer-readable media, one or more output devices (e.g., printer, display monitor, projector, speaker, etc.), a network controller and one or more input devices (e.g., keyboard, mouse, touch screen, gesture and/or voice recognition module, etc.). Non-transitory computer-readable media may include random access memory (RAM), read only memory (ROM), magnetic floppy disk, flash memory, and other types of memories, or a combination thereof. Other support circuits, such as a cache, a power supply, clock circuits and a communications bus, may also be provided in the computer system.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein may be implemented as computer-readable program code tangibly embodied in non-transitory computer-readable media of the computer system. As such, the computer system is a general-purpose computer system that becomes a specific-purpose computer system when executing the computer-readable program code.

Figure 1B:
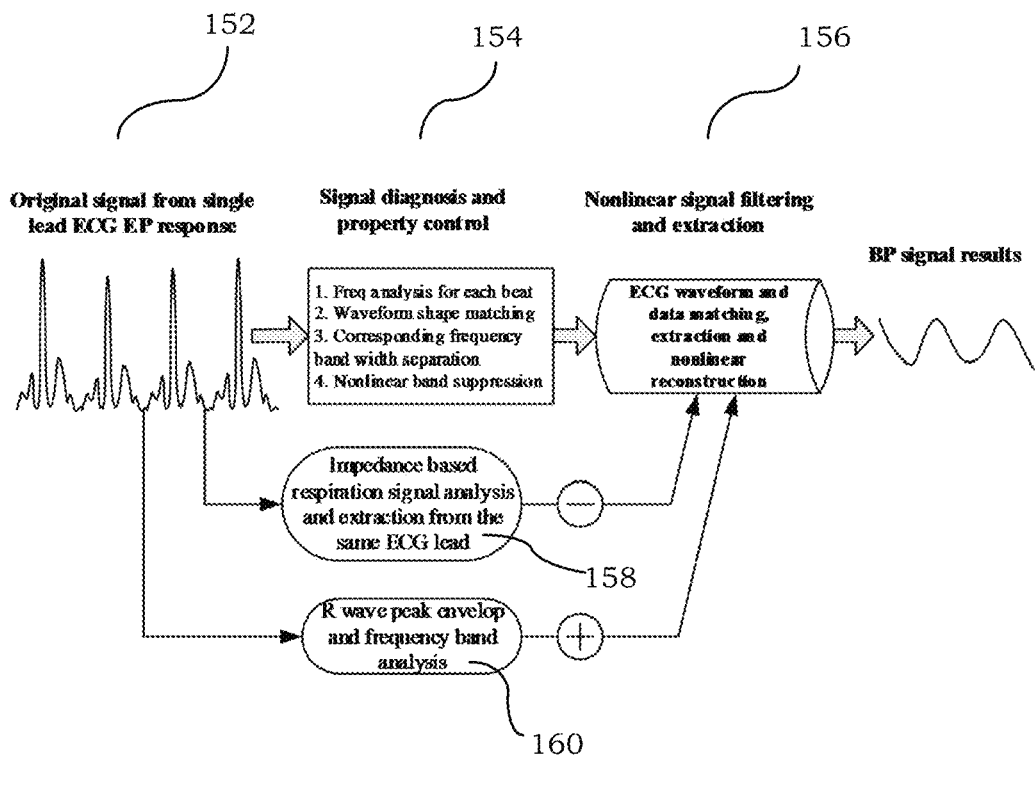
FIG. 1b illustrates an exemplary method of extracting blood pressure signals.

FIG. 1b illustrates an exemplary method of extracting blood pressure signal components 150 that may be implemented by exemplary system 100. The blood pressure signal components may be extracted from an original surface ECG signal 152 acquired from a single lead ECG EP response. At 154, signal diagnosis and property control is performed. For example, filter module 106 may perform frequency analysis for each heartbeat, waveform shape matching, corresponding frequency bandwidth separation and nonlinear bandwidth suppression.

At 158, filter module 106 extracts the real-time respiration impedance signal from the lead impedance measurement, so as to eliminate the respiration signal component from the patient signals. The respiration impedance signal may be estimated by unwanted signal estimator 113. At 160, filter module 106 may further extract the R wave peak envelop from the acquired patient signal to highlight the potential blood pressure signal categorization.

At 156, intermediate signal extraction module 114 may then perform frequency analysis and waveform segmentation in the frequency domain to generate an intermediate signal, such as an intermediate blood pressure (BP) signal. The intermediate BP signal may be derived by using data waveform matching and nonlinear signal reconstruction from preferred signal frequency sub-bands that do not have unwanted ECG signal components as well as other biological noises estimated by unwanted signal estimator 113. In some clinical cases, clean-up filter 120 may apply a smoothing and cleanup filtering to the intermediate BP signal to generate the final BP signal.

Figure 2:
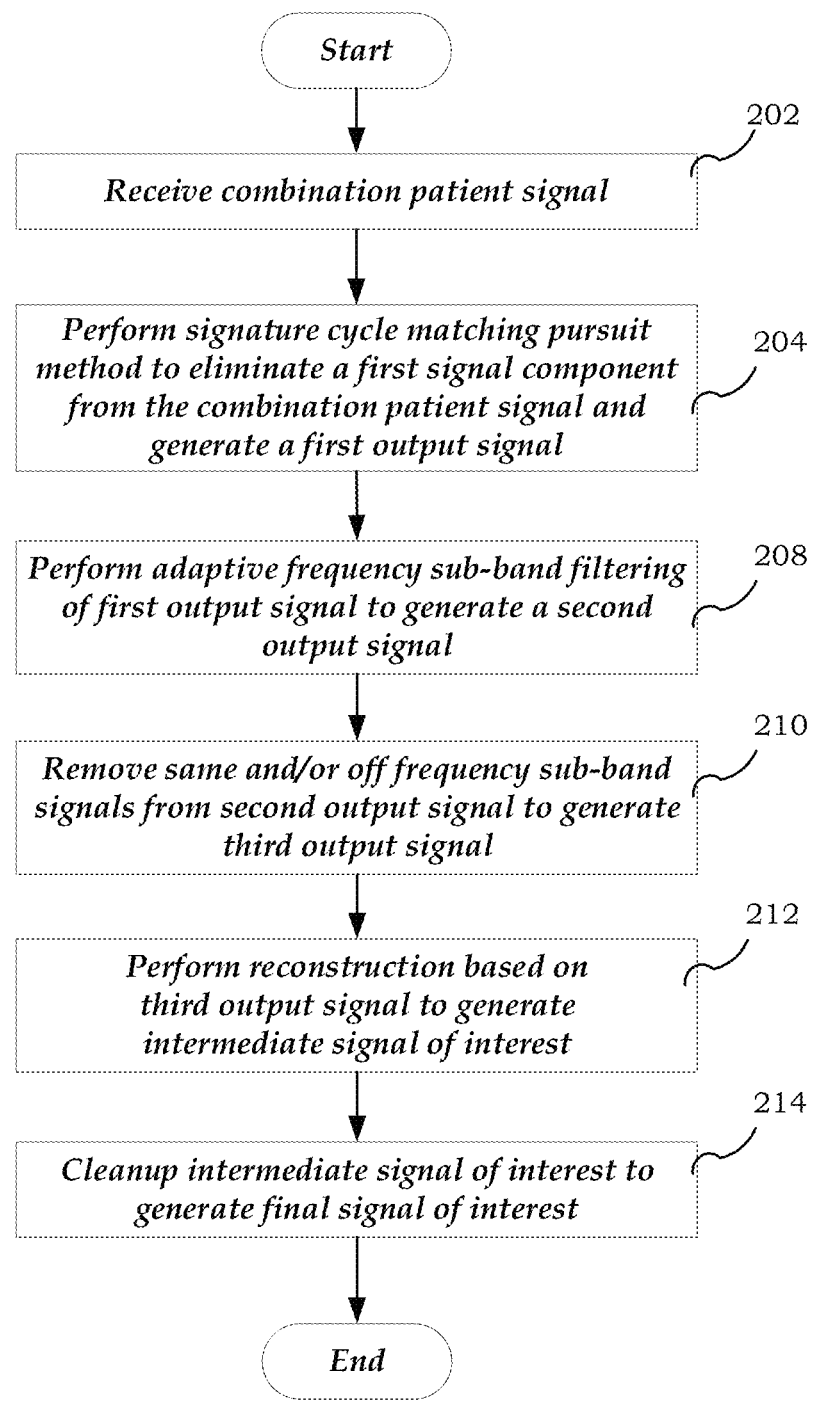
FIG. 2 illustrates an exemplary method of extracting a signal of interest from a combination patient signal.

FIG. 2 illustrates an exemplary method 200 of extracting a signal of interest (e.g., blood pressure signal) from a combination patient signal. The steps of the method 200 may be performed in the order shown or a different order. Additional, different, or fewer steps may be provided. Further, the method 200 may be implemented with the system 100 of FIG. 1a, a different system, or a combination thereof.

At 202, filter module 106 receives a combination patient signal from signal source 102. As discussed previously, the combination patient signal may include multiple patient signal and/or noise components from which process 200 may extract a signal of interest. The signal of interest is any signal component that has been identified for further analysis, such as a blood pressure signal component. Exemplary signal components include, but are not limited to, responses from different parts of the body, such as ECG signal from heart and muscle system, blood pressure signal from the blood flow force in the blood vessel, respiration signal from lung and muscle contraction, etc. An exemplary combination patient signal may be described by the following equation:

$$\text{signal} = BP \oplus ECG \oplus RESP \oplus + \text{noise} \oplus \qquad (1)$$

wherein signal denotes the combination patient signal, BP denotes the blood pressure signal component, ECG denotes the electrocardiogram (ECG) signal component, RESP denotes the respiration signal component, and noise denotes a noise component.

In most clinical cases, the amplitude and energy of each signal component in the acquired patient signal data depend on the type and position of the sensor used to acquire the patient signal data. This means that the ratio of the signal component amplitudes may vary due to the sensor type and position. For example, the electrophysiological activity response amplitude is much bigger than the amplitude of the respiration signal acquired from the electrical lead system, while the blood pressure signal amplitude is more dominant than the amplitude of the bipolar intra-cardiac EP response in an invasive cardiac signal acquired by using cardiac hemodynamic catheters and transducers.

At 204, filter module 106 performs a signature cycle matching pursuit method to eliminate a first signal component from the combination patient signal and generate a first output signal. The signature cycle matching pursuit method includes deriving a signature cycle (e.g., ECG signature cycle) from the combination patient signal, and removing the signal component associated with the signature cycle (e.g., ECG signal component) from the combination patient signal to generate a first output signal. In some implementations, an ECG signal component is removed to more accurately and reliably extract the signal of interest (e.g., blood pressure signal component) from the ongoing combination patient signal. However, it may be a challenge to efficiently eliminate the ECG signal component due to at least two reasons: (a) the ECG signal amplitude is larger than amplitudes of other signals, especially those acquired from the surface lead system; and (b) ECG signal component usually has a pretty broad frequency bandwidth (e.g., 3 Hz to 250 Hz) compared to the blood pressure bandwidth (0.5 Hz to 50 Hz), which means normal bandwidth filters (e.g., low pass, high pass and band pass filters) may not be able to effectively separate the blood pressure signal from ECG activity and response.

In some implementations, unwanted signal estimator 113 derives the signature cycle from the combination patient signal by selecting the reference portion episode (e.g., typical part in the ECG signal recording) and using an average heart beat cycle as the signature cycle. Filter module 106 then filters out or eliminates the signal component associated with the signature cycle from the combination patient signal by synchronizing the timing of the signature cycle in the acquired patient signals to generate the first signal.

Figure 3:
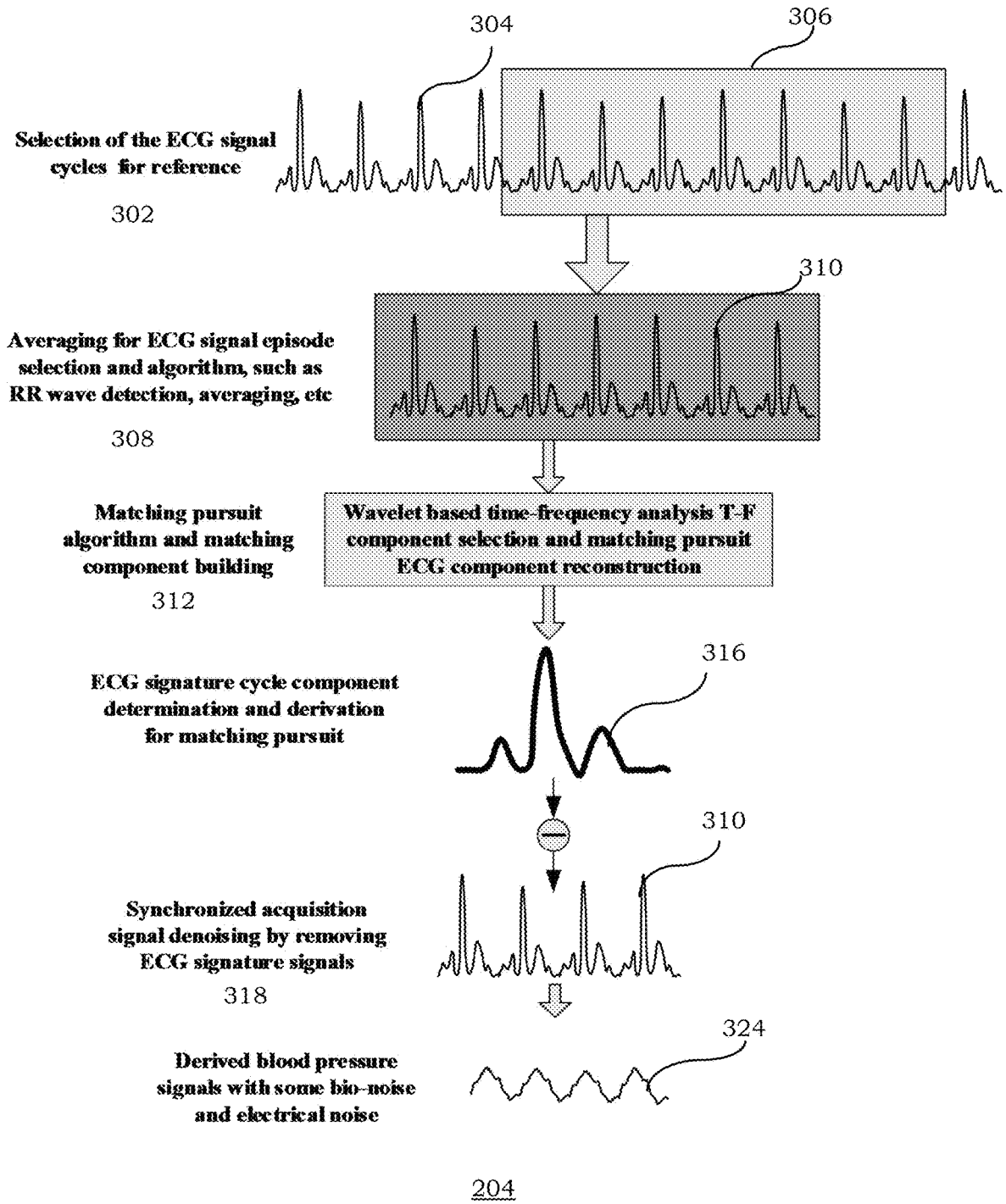
FIG. 3 illustrates an exemplary ECG signature cycle matching pursuit method.

FIG. 3 illustrates an exemplary ECG signature cycle matching pursuit method 204 for deriving and eliminating the ECG signal component from the ongoing combination patient signal 304 acquired from a patient surface lead system. At step 302, reference cycles of the combination patient signal 304 may be selected within a calculation window 306. The average size of the calculation window 306 may be, for example, 10 to 20 heart beat cycles. At 308, averaging may be performed on the reference cycles within the calculation window 306 to remove white noise (e.g., environmental noise) and periodic signal components (e.g., respiration signal components) to generate averaged signal cycles 310. Averaging may be performed by RR wave detection, which facilitates cycle segmentation. The detected R waves may be used for cycle averaging, selection of different signal portions, etc.

The ECG and blood pressure signal components are usually at the same rate and cannot be separated by averaging. Fortunately, ECG and blood pressure signal components occur at different timing stamps, even though the spectral frequencies are sometimes in the same frequency bandwidth. Therefore, the ECG signature cycle may be calculated by performing a time-frequency matching pursuit and reconstruction method at step 312. Wavelet-based time-frequency (T-F) distribution analysis may be used to reconstruct the ECG signature cycle 316. It should be appreciated that other methods may also be used to identify the ECG signal signature cycle.

Figure 4:
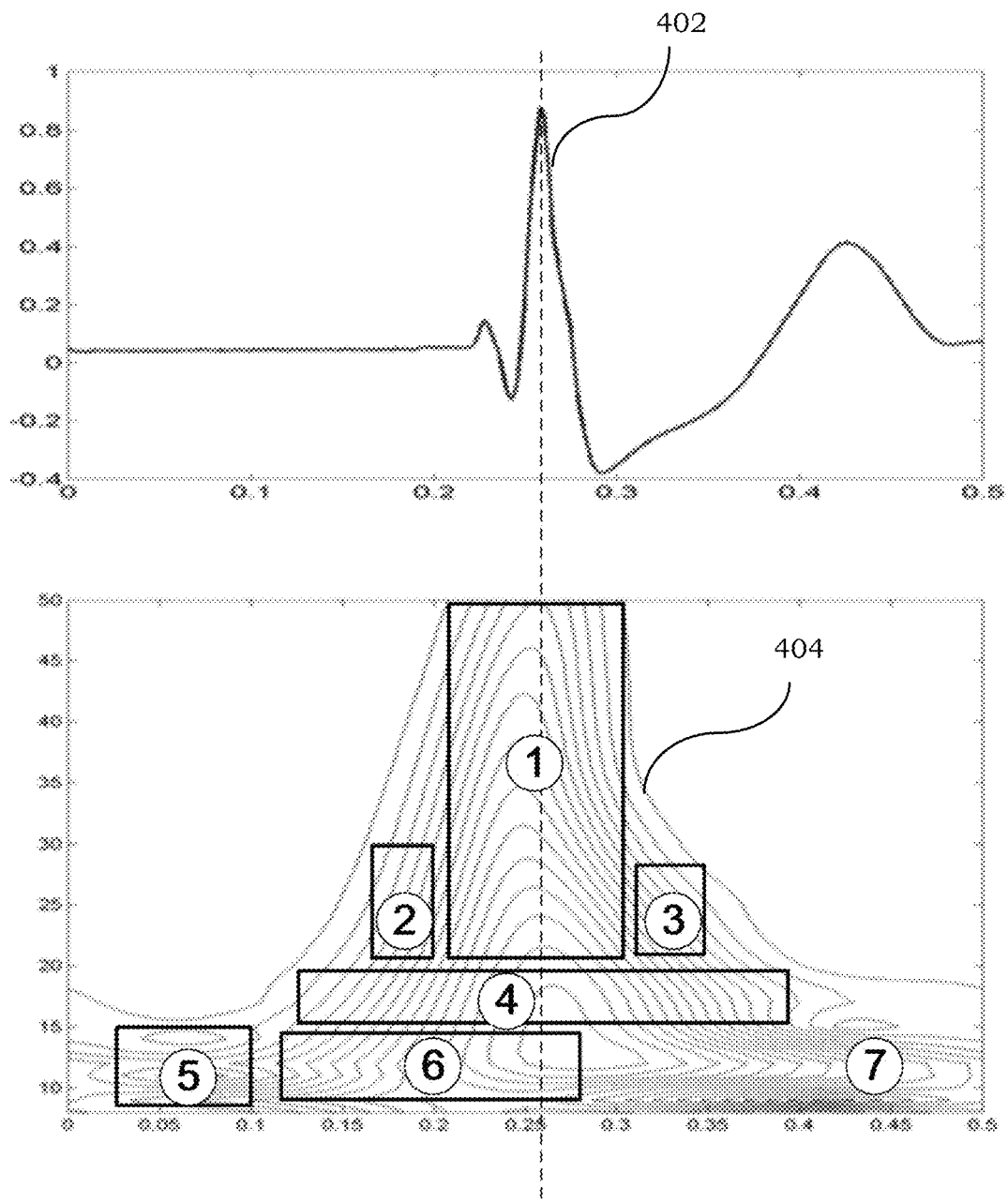
FIG. 4 shows a computer simulation of an ECG signal and corresponding time-frequency (T-F) distribution.

More particularly, the wavelet-based T-F matching pursuit method may be used to select ECG signature cycle sub-components, which are also used for reconstructing ECG signature cycle 316. FIG. 4 shows a computer simulation of an ECG signal 402 and corresponding time-frequency (T-F) distribution 404. Various clinically significant sub-components (#1 to #7) of the T-F distribution 404 may be segmented based on T-F distribution analysis. The sub-components (#1 to #7) may be segmented based on, for example, prior knowledge of the ECG signal (e.g., energy and waveform distribution of the P wave, QRS wave, etc.).

In some implementations, a 6-layer wavelet decomposition is applied to generate the ECG signature cycle sub-components. According to the position and clinical significance, the sub-components may be marked #1 to #6 to be used for ECG signature component reconstruction. Sub-component #7 may be eliminated and not used for reconstructing the ECG signature component. Clinically significant sub-components #1 to #6 may be adaptively selected by a clinical user or software program, such as a timing-duration and frequency range determination algorithm. The selected sub-components #1 to #6 may then be used to reconstruct a new ECG signal component (i.e., ECG signature cycle), which can be used in the matching pursuit analysis in the blood pressure signal extraction and unwanted signal/noise removal step 318 as shown in FIG. 3.

Returning to FIG. 3, at step 318, signal 310 is denoised by removing the ECG signature signal cycle 316 to generate intermediate blood pressure signal component 324 (or first output signal). This may be performed by comparing and synchronizing the ECG signature cycle with each cardiac cycle. In some implementations, the ECG signature cycle is synchronized with the R wave of each cardiac cycle. The resulting intermediate blood pressure signal component 324 (or first output signal) may still include some biological and/or electrical noise.

Returning to FIG. 2, at 208, filter module 106 performs frequency sub-bandwidth filtering of the first output signal to generate a second output signal. Such sub-bandwidth filtering may be linear or non-linear. Linear filtering generally involves processing an input signal to produce an output signal subject to a linearity constraint (i.e., straight line relationship), while nonlinear filtering generally involves producing an output signal that is not a linear function of the input signal. In nonlinear filtering, the filter parameters (e.g., bandwidth, amplitude threshold, coefficients, etc.) may be non-uniformly segmented based on signal characteristics, and nonlinearly controlled and adaptively adjusted by software or the clinical user.

Filter parameters may be adaptively adjusted to remove one or more unwanted signal components (e.g., noise) in response to changes in the second output signal. As discussed previously, the ECG signature component can be eliminated by using the signature cycle matching pursuit method on the ongoing acquired combination patient signal (or from a pre-defined benign signal episode or reference signal portion). However, due to resolution and signal accuracy limitations, it may not be possible to completely eliminate remaining noise and unwanted artifacts. In addition, blood pressure signal components, in addition to other patient signal components, may sometimes show time-varying changes. Therefore, a varying signal frequency bandwidth control based on ongoing signal characteristics for filtering may be needed.

Figure 5:
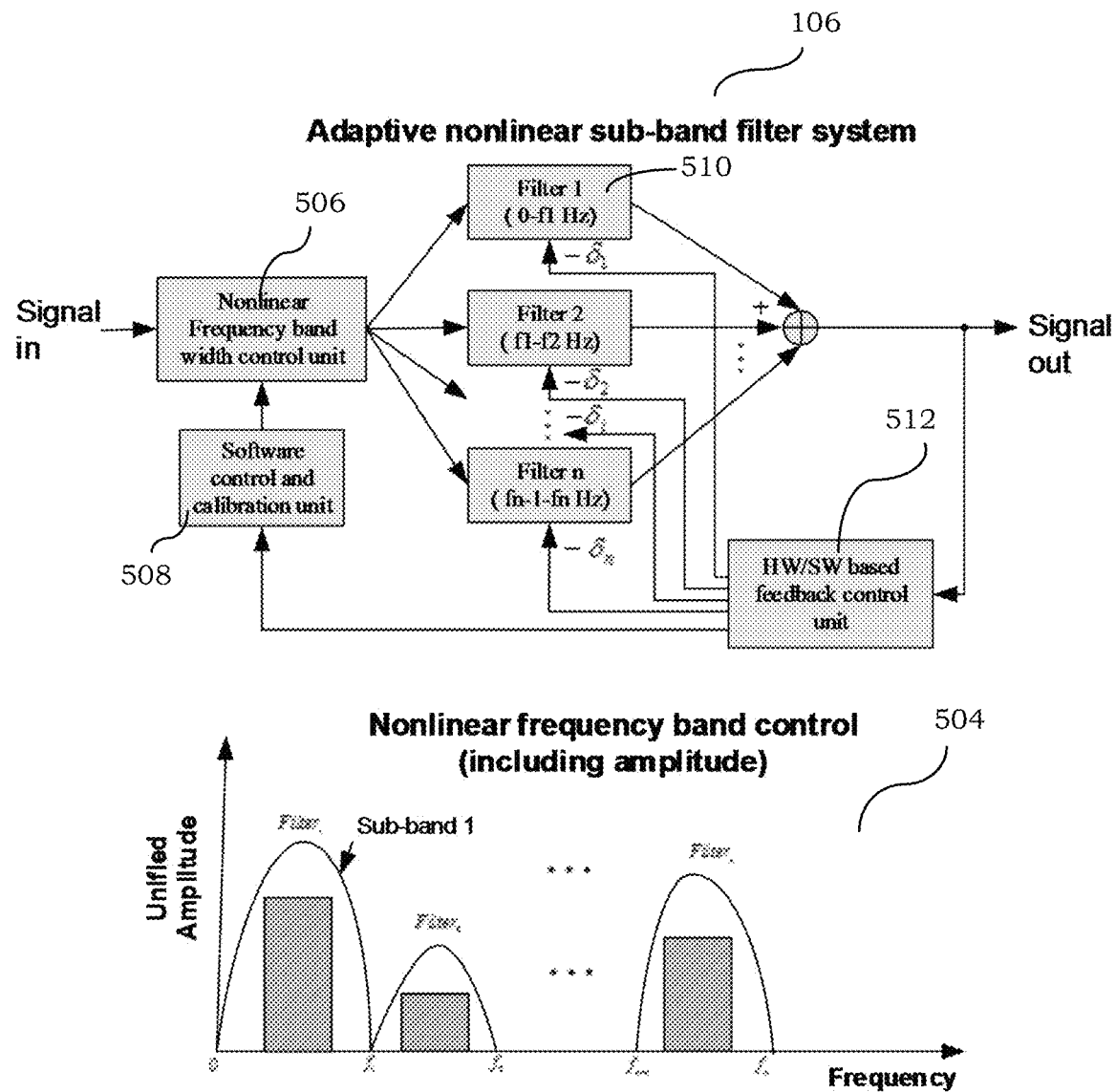
FIG. 5 illustrates an exemplary method of nonlinear frequency bandwidth control.

FIG. 5 illustrates an exemplary method of nonlinear frequency bandwidth control. More particularly, an adaptive nonlinear sub-bandwidth (or sub-band) filter system 106 and a corresponding amplitude-frequency graph 504 are shown. The filter system 106 may include a nonlinear frequency bandwidth control unit 506 for controlling filters 1 to n (510). Nonlinear frequency bandwidth control unit 506 may include signal characterization algorithms implemented in software, hardware and/or firmware (e.g., FPGA and microcontroller) for controlling filter parameters. Exemplary filter parameters may include, for instance, size of frequency sub-bands, amplitude threshold of each sub-band, filter shape (e.g., filter order, rising-falling edge, etc.) of each sub-band, and so forth. Such filter parameters (frequency band size, cut-off frequency, amplitude threshold, filter order, etc.) may be automatically and adaptively tuned via signal calculation and diagnosis. These filter parameters and associated sub-band categorization may be nonlinear (or non-uniform) due to the nonlinear characteristics of the patient signal, such as IBP signal, ECG signals, etc.

Filters 1 to n (510) separates (or categorizes) the frequency bandwidth of the ongoing patient signal (or first output signal) into several frequency sub-bandwidths for various clinical purposes, as shown in the amplitude-frequency graph 504. The frequency sub-bandwidths may include, but are not limited to, low dynamic range for IBP signal component, middle range for ECG signal component, high range for ICEG signal component, etc. Each filter may separate the frequency bandwidth into a default frequency bandwidth, such as 0-5 Hz for filter 1, 5-10 Hz for filter 2, 10-16 Hz band filter 3, and so forth.

In some implementations, software control and calibration unit 508 is communicatively coupled to nonlinear frequency bandwidth control unit 506 for adaptively controlling the filters 1 to n (510) in substantially real-time. The filters 510 are adaptively controlled in response to changes in the output signal (Signal out) communicated via hardware (HW)/software (SW) based feedback control unit 512. Software control and calibration unit 508 may, for example, modify the number of filters, sub-bandwidth size (e.g., f1, f2, etc. frequency values) and other filter parameters (e.g., order, shape, amplification ratio, cut-off frequency, feedback coefficient $\delta_i$, etc.) associated with the filters 1 to n. Such adaptive controlling is responsive to the dynamic shifting and minute changes in the output signal, and is particularly useful in removing unwanted signals and/or noise that are located in frequency bandwidths that are different from preferred signals (or signals of interest) that need to be admitted. The filter parameters may be modified to best fit the current patient situation and/or clinical application requirements. When preferred signals and unwanted signals and/or noise have overlapping frequency bandwidths, partial signals may help increase the signal-to-noise ratio. However, admitting some unwanted signal or noise may help to retain most of preferred signals, and signal smooth filtering may be employed to eliminate the unwanted noise from the overlap of frequency bandwidths.

The filter parameters may be automatically adjusted by using different approaches, such as fuzzy algorithms, expert algorithm, etc. In some implementations, an artificial neural network (ANN)-based method is used to determine the filter parameters. In addition, the ANN-based method may also derive other control parameters, such as a reference-benign signal, size of shifting window, etc.

Figure 6:
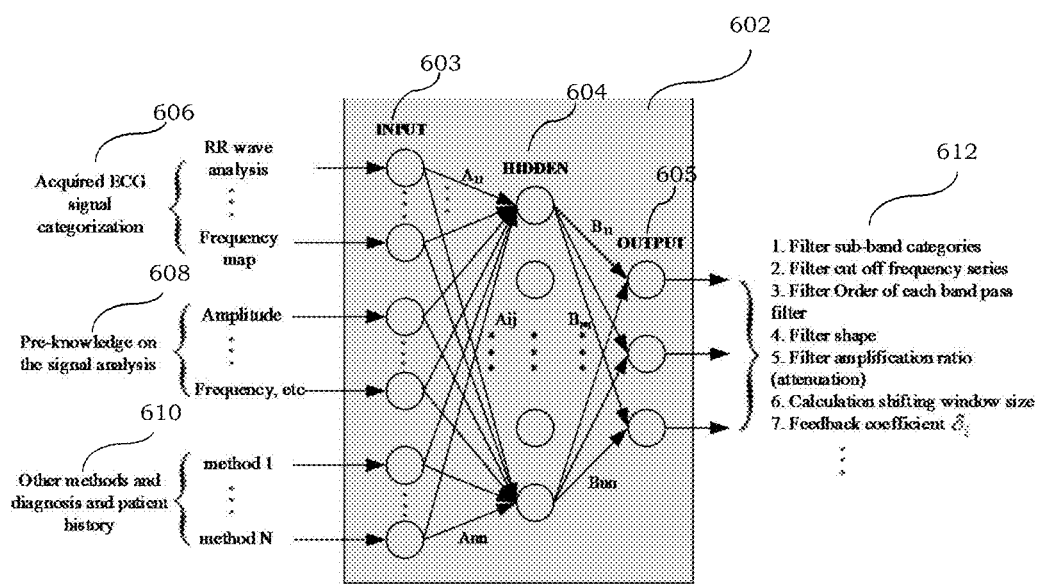
FIG. 6 shows an exemplary artificial neural network (ANN) module.

FIG. 6 shows an exemplary ANN module 602 for non-linearly estimating filter parameters and associated control parameters. The exemplary ANN module 602 includes three layers: input layer 603, hidden layer 604 and output layer 605. $A_{ij}$ are weights applied between the input layer 603 and hidden layer 604, while $B_{pq}$ are weights applied between the hidden layer 604 and output layer 605. $A_{ij}$ weights and $B_{pq}$ weights can be adaptively adjusted with a training data set. ANN unit 602 may incorporate a self-learning function that processes new input data 606, 608 and 610 to increase the precision and accuracy of calculated results 612.

ANN module 602 combines and maps input data 606, 608 and 610 to output parameters 612. Exemplary input data includes data associated with acquired ECG signal categorization 606 (e.g., RR wave analysis results, frequency map, etc.), data associated with pre-knowledge of signal analysis 608 (e.g., amplitude, frequency, etc.) and data associate with other methods and patient history (e.g., method 1 to N). Depending on the application and clinical usage (e.g., convenience, precision, etc.), methods 1 to N may correspond to different stages, different frequency bandwidths, different parameters, etc. Exemplary output parameters may include, but are not limited to, filter sub-band categories, filter cut-off frequency series, filter order of each band pass filter, filter shape, filter amplification ratio (or attenuation), calculation shifting window size, feedback coefficient $\delta_i$ and so forth.

Returning to FIG. 2, at 210, filter module 106 removes same and/or off sub-bandwidth signal components from second output signal to generate a third output signal. Such signal components are within the same frequency sub-bandwidth and/or outside the frequency sub-bandwidth of the signal of interest (e.g., blood pressure signal component). Off frequency sub-band signal components may include a respiration signal component, while same frequency sub-bandwidth signal components may include other unwanted noise (e.g., power line or electrical noise).

The respiration signal component may be extracted by RR waveform peak envelop diagnosis. Typically, the respiration signal component is much slower than the ECG signal component, and actually continuously and dynamically shift the signal base. When the signal source 102 records an ECG signal, it is actually recording a modulated ECG signal with a low frequency waveform shifting respiration signal component. By tracking the amplitudes and positions of the R waves, the respiration signal component may be extracted from the R waves. For simplification, the respiration signal component can be eliminated by adaptive low pass filtering, such as 0.5 to 3 Hz, which corresponds to the respiration rate of 2 to 180 per minute. By defining the frequency range, the respiration signal component can be separated.

Same frequency bandwidth signal separation may be performed to eliminate power line and electrical noise from other medical devices (via Electromagnetic compatibility or EMC and electromagnetic interference or EMI) from the patient signal. Such noise components may be within the frequency range of 50-60 Hz and their harmonics, such as 100 Hz, 120 Hz, etc. These unwanted noise frequency ranges are within the signal bandwidth as the blood pressure signal component, and some sharp notch filtering may be needed. These notch filters may have high Q value and adaptive center peak frequency tracking, such as from 59 to 61 Hz (for 60 Hz power line noise).

At 212, intermediate signal extraction module 114 performs reconstruction of the signal of interest (e.g., blood pressure signal component) from the third output signal to generate an intermediate signal of interest. After removing the first signal component (e.g., ECG signal component), the same and/or off frequency sub-bandwidth signals (e.g., respiration signal component, noise, etc.), the resulting third output signal may still be categorized into different predetermined sub-bands by using adaptive frequency bandwidth filtering. A time-varying weighted signal reconstruction approach may be used to integrate the sub-band components which have been filtered in step 208.

Figure 7:
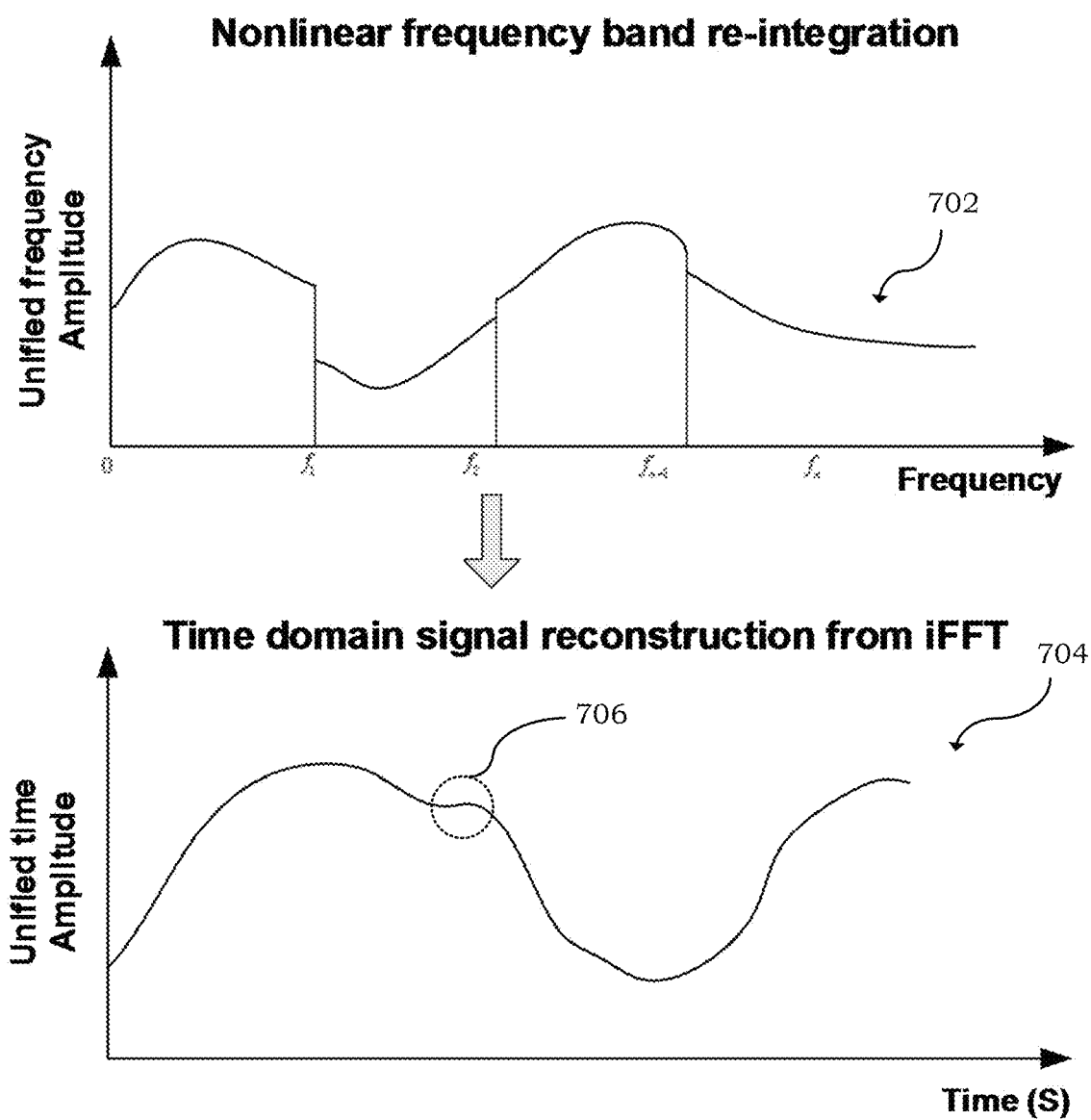
FIG. 7 illustrates an exemplary method of blood pressure signal reconstruction from nonlinear frequency sub-bands.

FIG. 7 illustrates an exemplary method of blood pressure signal reconstruction from nonlinear frequency sub-bands. A unified frequency amplitude versus frequency graph 702 is shown to illustrate the re-integration (or addition) of different filter sub-bands in the frequency domain. A unified frequency amplitude versus time graph 704 is shown to illustrate the reconstruction of a blood pressure signal in the time domain by performing inverse fast Fourier transform (IFFT) on the integrated frequency components. Due to the gap between the integrated frequency sub-components, the reconstructed blood pressure signal may show some unexpected peaks or artifacts 706. These nonlinear gap noise or artifacts may be eliminated by signal smooth filtering, as will be described with reference to step 214. In some implementations, the nonlinear gaps or non-smooth frequency connection points between different filter frequency bands are interpolated, especially at the cut-off frequency points. By using interpolation to bridge the gap points, the whole frequency spectrum waveform may be much smoother with all the unwanted fast changing points removed to generate an intermediate blood pressure signal.

At 214, cleanup filter 120 cleans up the intermediate signal of interest to remove artifacts and generate the final signal of interest. Signal shape clean-up or smooth filtering may be used as a denoising method for reconstructed blood pressure waveforms, which still contain a lot of fast changing signal components due to noise or artifact accumulation. Shape cleanup or smooth filtering method is based on the assumption that biological signals do not change too fast. If there is any fast change within the patient signal, it is considered to be some kind of noise that should be discarded.

In some implementations, Savitzky-Golay smoothing filters are used. Such smoothing filter may also be referred to as digital smoothing polynomial filters or least-squares smoothing filters. Compared with standard averaging infinite impulse response (IIR) and finite impulse response (FIR) filters, Savitzky-Golay smoothing filters perform much better by filtering out a significant portion of the signal's high frequency content along with the noise. Savitzky-Golay smoothing filters are optimal in the sense that they minimize the least-squares error in fitting a polynomial to each frame of noisy data. The signal-to-noise ratio (SNR) may be improved from 1:10 to final 20:1 after the signal cleanup and smooth filtering. Usually, when the signal to noise is 1:10, the blood pressure signal is not clearly visible, while the blood pressure signal has very good shape and resolution once the SNR is 20:1.

Figure 8:
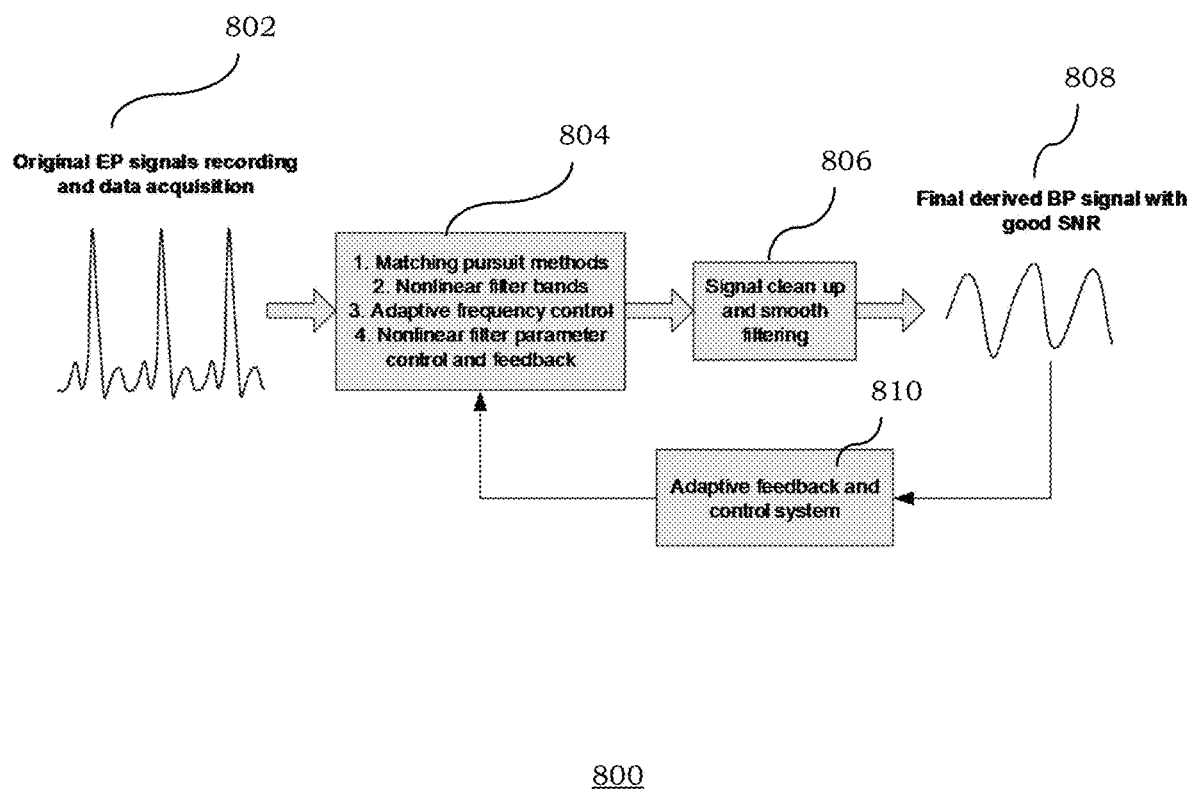
FIG. 8 illustrates an exemplary computer data simulation of one implementation of the present method of blood pressure signal extraction from electrophysiological (EP) signals.

One aspect of the present framework provides an indirect approach to extract blood pressure signal component that is buried inside the EP signal data. FIG. 8 illustrates an exemplary computer data simulation of one implementation of the present method of blood pressure signal extraction from EP signals. This example may provide evidence that it is possible to extract blood pressure signal from any patient signal recording. This may save a lot of clinical effort, analysis and patient risk, advantageously removing the need to use multiple transducers and medical equipment.

The data simulation example shows blood pressure signal extraction from real-time LA lead electrophysiological signal data 802 acquired from an intra-cardiac catheter. The blood flow and myocardium electrical characteristics varied with heart cycles, which resulted in intra-cardiac myocardial and blood fluid impedance changes. The blood pressure changes corresponded to the impedance changing rate and mode. In the original EP signal data 802, there was nearly no way to visualize the blood pressure signal component. After applying the present techniques 804 (e.g., matching pursuit method, sub-bandwidth filtering, adaptive frequency control and nonlinear filter parameter control and feedback), as well as signal clean-up and smooth filtering 806, the resulting BP signal 808 was very obvious. An adaptive feedback and control system 810 was used to control the filter parameters in response to changes in the resulting BP signal 808, thereby optimizing the SNR to meet the requirements of the application. In the resulting BP signal 808, all ECG signal components, power line noise and other biological noise, were eliminated and signal-to-noise ratio (SNR) was roughly 23:1.

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

The invention claimed is:

1. A non-transitory computer readable medium having embodied thereon computer-executable instructions which, when executed, cause a computer to perform steps for signal filtering, the steps comprising:
   receiving an electrocardiogram signal, wherein the electrocardiogram signal includes an electrocardiogram signal component, noise, a respiration signal component and a blood pressure signal component;
   removing the electrocardiogram signal component from the electrocardiogram signal to generate a first output signal by performing an electrocardiogram signature cycle matching pursuit method;
   eliminating the noise from the first output signal to generate a second output signal by performing sub-bandwidth filtering of the first output signal;
   removing the respiration signal component from the second output signal to generate a third output signal; and
   reconstructing a time-domain blood pressure signal based on the third output signal by performing inverse fast Fourier transform (IFFT) on integrated frequency components of the third output signal.

2. The non-transitory computer readable medium of claim 1 having embodied thereon further computer-executable instructions which, when executed, cause the computer to perform the electrocardiogram signature cycle matching pursuit method by deriving a signature cycle from the electrocardiogram signal and removing the electrocardiogram signal component associated with the signature cycle from the electrocardiogram signal.

3. The non-transitory computer readable medium of claim 2 having embodied thereon further computer-executable instructions which, when executed, cause the computer to perform the sub-bandwidth filtering of the first output signal by performing steps comprising:
   separating, via multiple filters, the first output signal into multiple frequency sub-bandwidths to generate the second output signal; and
   adaptively adjusting, in response to changes in the second output signal, filter parameters associated with the filters to remove the noise.

4. The non-transitory computer readable medium of claim 1 having embodied thereon further computer-executable instructions which, when executed, cause the computer to remove the respiration signal component by low pass filtering.

5. The non-transitory computer readable medium of claim 1 having embodied thereon further computer-executable instructions which, when executed, cause the computer to clean up the blood pressure signal by applying a Savitzky-Golay smoothing filter.

6. A method of signal filtering, comprising:
   receiving an electrocardiogram signal that includes first, second, third signal components and a signal component of interest;
   removing the first signal component from the electrocardiogram signal to generate a first output signal by performing a signature cycle matching pursuit method based on the electrocardiogram signal, wherein performing the signature cycle matching pursuit method includes
      selecting, from the electrocardiogram signal, reference cycles,
      averaging the reference cycles to generate averaged signal cycles,
      deriving a signature cycle from the averaged signal cycles, and
      removing the first signal component associated with the signature cycle from the electrocardiogram signal;
   removing the second signal component from the first output signal to generate a second output signal by performing linear sub-bandwidth filtering of the first output signal;
   removing the third signal component from the second output signal to generate a third output signal; and
   reconstructing a signal of interest in time domain based on the third output signal by performing inverse fast Fourier transform (IFFT) on integrated frequency components of the third output signal.

7. The method of claim 6 wherein the electrocardiogram signal comprises a blood pressure signal component, an electrocardiogram signal component, a respiration signal component and a noise component.

8. The method of claim 7 wherein the signal of interest is a blood pressure signal component.

9. The method of claim 6 wherein removing the first signal component associated with the signature cycle from the electrocardiogram signal comprises synchronizing the signature cycle with an R wave of at least one cycle of the electrocardiogram signal.

10. The method of claim 6 wherein the signature cycle comprises an electrocardiogram signature cycle.

11. The method of claim 6 wherein deriving the signature cycle comprises:
reconstructing the signature cycle by performing a wavelet-based time-frequency distribution analysis.

12. The method of claim 11 wherein performing the wavelet-based time-frequency distribution analysis comprises:
segmenting a time-frequency distribution of the signal component into a set of sub-components;
selecting, based on time duration and frequency range determination, a sub-set of six clinically significant sub-components from the set of sub-components; and
reconstructing the signature cycle based on the sub-set of the six clinically significant sub-components.

13. The method of claim 6 wherein performing the sub-bandwidth filtering of the first output signal comprises:
separating, via multiple filters, the first output signal into multiple frequency sub-bandwidths to generate the second output signal; and
adaptively adjusting, in response to changes in the second output signal, filter parameters associated with the filters to remove the second signal component.

14. The method of claim 13 wherein the filter parameters comprise a number of filters, bandwidth size, order, shape, amplification ratio, cut-off frequency, or a combination thereof.

15. The method of claim 13 wherein adaptively adjusting the filter parameters comprises performing an artificial neural network-based method.

16. The method of claim 6 wherein removing the third signal component from the second output signal comprises removing a respiration signal component by performing low pass filtering.

17. The method of claim 6 further comprises cleaning up the signal of interest by applying a Savitzky-Golay smoothing filter.

* * * * *